United States Patent [19]

Olafson

[11] Patent Number: 5,674,503
[45] Date of Patent: Oct. 7, 1997

[54] PEPTIDES CAPABLE OF ELICITING AN IMMUNE RESPONSE TO LEISHMANIASIS AND METHODS OF USING THE SAME

[75] Inventor: Robert W. Olafson, Victoria, Canada

[73] Assignee: University of Victoria, Victoria, Canada

[21] Appl. No.: 310,207

[22] Filed: Sep. 21, 1994

Related U.S. Application Data

[63] Continuation of Ser. No. 970,226, Nov. 2, 1992, abandoned, which is a continuation of Ser. No. 558,009, Jul. 24, 1990, abandoned.

[51] Int. Cl.$^6$ .................. A61K 39/008; A61K 38/00; A61K 38/04; C07K 14/44
[52] U.S. Cl. .................. 424/269.1; 424/184.1; 424/185.1; 530/324; 530/325; 530/326; 530/327; 530/300
[58] Field of Search .................. 424/184.1, 185.1, 424/269.1; 530/326, 327, 324, 325, 300

[56] References Cited

PUBLICATIONS

Medina–Acoster Mol. & Bioch. Paras 37:263–274 1989.
Russell et al The J. of Imm 140:1274–1279 Feb. 1988.
Button et al the J. of Exp Med. "The Molecular Cloning of the Major Surface Antigen of Leishmania." vol. 167:724–729 1988.
Margalit et al The Journ of Imm. 138:2213–2229, 1987 Prediction of Immunodominant Helper T Cell Antigenic Sites From the Primary Sequence.
Brot et al Archives of Biochem & Biophysics, 223:271–281 1983, "Biochemistry & Physiological Role of Melhroune Sulfoxide Residues in Proteins".
Rothbard and Taylor, EMBO Journal 7:93–100 1988, "A Sequence Pattern Common to T–Cell Epitopes".
Russell et al, The J. of Imm. 140:1274–1279, 1985, Effective Immunization Against Cutaneous Leishmaniasis in the Defined Membrane Antigen Reconstituted into Liposomes.
Modabben Parasitology 98:S49–S60, 1989 Expreiences with Vaccines Against Cutaneous Leishmaniasis of Mice & Men.
Clark The Journ. of Immun. 2725–2725 vol. 129, 1982 "Chemotactic Factors Trigger Their Own Oxidative Inactivation by Human Neutrophils".
Clark et al The Journ of Imm. 126:1507–1513, 1982 Chemotactic Factor Inactivation by Stimulated Human Neutrophils Mediated by Myeloperoxidase–Catalyzed Melhionine Oxidation.
Stryer, Biochemistry p. 15, 2nd Ed copy 1975, 1981.
Kumar et al, PNAS 87:1337–1341 1990. Amino Acid Variations at a Single Residue in an Autoimmune Peptide Profoundly Affect its Properties: T–Cell Activator, Major Histocompatibility Complex Binding & Ability to Block Experim.
Chaudhuri et al., "Surface Acid Proteinase (gp63) of *Leishmania mexicana,*" *J. Biol. Chem.* 264(13):7483–7489, 1989.
Hill et al., "Elimination of CD4 $^+$Suppressor T Cells From Susceptible BALB/C Mice Releases CD8$^+$ T Lymphocytes to Mediate Protective Immunity Against Leishmania," *J. Exp. Med.* 169:1819–1827, 1989.

Reiner et al., "Genetic Heterogeneity in Peruvian Leishmania Isolates," *Am. J. Trop. Med. Hyg.* 41(4):416–421, 1989.
Farrell et al., "A Role for LYT–2 $^+$T Cells in Resistance to Cutaneous Leishmaniasis in Immunized Mice," *J. Immunology* 142(6):2052–2056, 1989.
Liew et al., "Prophylactic Immunization Against Experimental Leishmaniasis: VI. Comparison of Protective and Disease–Promoting T Cells," *J. Immunology* 139(9):3112–3117, 1987.
Mitchell and Handman, "The Glyconjugate Derived From a *Leishmania major* Receptor for Macrophages Is a Suppressogenic, Disease–Promoting Antigen in Murine Cutaneous Leishmaniasis," *Parasite Immunology* 8:255–263, 1986.
Handman and Mitchell, "Immunization with Leishmania Receptor for Macrophages Protects Mice Against Cutaneous Leishmaniasis," *Proc. Natl. Acad. Sci. USA* 82:5910–5914, 1985.
Liew et al., "Prophylactic Immunization Against Experimental Leishmaniasis: IV. Subcutaneous Immunization Prevents the Induction of Protective Immunity Against Fatal *Leishmania major* Infection," *J. Immunology* 135(3):2095–2101, 1985.
Liew et al., "Prophylactic Immunization Against Experimental Leishmaniasis: V. Mechanism of the Anti–Protective Blocking Effect Induced by Subcutaneous Immunization Against *Leishmania major* Infection," *J. Immunology* 135(3):2102–2107, 1985.
Dhaliwal et al., "Specific Suppressor T Cells for Delayed–Type Hypersensitivity in Susceptible Mice Immunized Against Cutaneous Leishmaniasis," *Infection & Immunity* 49(2):417–423, 1985.
Liew et al., "Prophylactic Immunization Against Experimental Leishmaniasis: III. Protection Against Fatal *Leishmania tropica* Infection Induced by Irradiated Promastigotes Involves LYT–1$^+$2$^-$ T Cells that Do Not Mediate Cutaneous DTH," *J. Immunology* 132(1):456–461, 1984.
Koufman et al., "Observations on Immunization Against Cutaneous Leishmaniasis in Israel," *Israel J. Med. Sci.* 14(2):218–222, 1978.
McMaster et al., "Molecular Genetics of the Major Glycoprotein and Repetitive Antigens of Leishmania," *Parasites: Molecular Biology, Drug and Vaccine Design* O 013, p. 69.
Button et al., "Expression in *Escherichia coli* of Genes Encoding the Major Surface Glycoprotein From Leishmania," *Parasites: Molecular Biology, Drug and Vaccine Design* O 408, p. 99.
Webb et al., "Comparison of the Genomic DNA Sequence Enconding the Cell Surface Glycoprotein Gp63 of *Leishmania major* and *L. donovani,*" *Parasites: Molecular Biology, Drug and Vaccine Design* O 488, p. 126.
Titus et al., "Induction of Resistance to Experimental Cutaneous Leishmaniasis in Genetically–Susceptible BALB/C Mice by Immunization with Chemically–Mutagenized Non–Infective Clones of *Leishmania major,*" *Microbial–Immune Response Interactions III* (3436–3441), 3436, A887.

*Primary Examiner*—Hazel F. Sidberry
*Attorney, Agent, or Firm*—Seed and Berry LLP

[57] ABSTRACT

The present invention provides immunogens suitable for vaccination against leishmaniasis.

8 Claims, 5 Drawing Sheets

Primary Structure of Mature L. Major gp63

```
     PT1      10         20         30         40         50
      VRDVNWGALRIAVSTEDLTDPAYHCARVGQHVKDHAGAIVTCTAEDILTN

PT2 60   PT9 70         80         90        100
      EKRDILVKHLIPQAVQLHTERLKVQQVQGKWKVTDMVGDICGDFKVPQAH 110       120   PT10 130        140        150
      ITEGFSNTDFVMYVASVPSEEGVLAWATTCQTFSDGHPAVGVINIPAANI

PT3    160  PT4 170        180        190   PT12 200
      ASRYDQLVTRVVTHEMAHALGFSGPFFEDARIVANVPNVRGKNFDVPVIN

PT12     210  PT13 220        230        240  PT14 250
      SSTAVAKAREQYGCDTLEYLEVEDQGGAGSAGSHIKMRNAQDELMAPAAA

260 PT15   270        280        290        300
      AGYYTALTMAIFGDLGFYQADFSKAEVMPWGDNAGCAFLTNKCMEQSVTQ 310        320        330        340        350
      WPAMFCNESEDAIRCPTSRLSLGACGVTRHPGLPPYWQYFTDPSLAGVSA 360        370   PT6 380    PT7 390    PT8 400
      FMDYCPVVVPYSDGSCTQRASEAHASLLPFNVFSDAARCIDGAFRPKATD
                      PT16

PT8      410        420        430        440        450
      GIVKSYAGLCANVQCDTATRTYSVQVHGSNDYTNCTPGLRVELSTVSNAF 460        470        480        490        502
      EGGGYITCPPYVEVCQGNVQAAKDGGNTAAGRRGPRAAATALLVAALLAVAL
                                                PT17
```

PEPTIDES CAPABLE OF ELICITING AN IMMUNE RESPONSE TO LEISHMANIASIS AND METHODS OF USING THE SAME

CROSS-REFERENCE TO RELATED APPLICATIONS

This application is a continuation of U.S. patent application Ser. No. 07/970,226, filed Nov. 2, 1992, now abandoned, which is a continuation of U.S. application Ser. No. 07/558,009, filed Jul. 24, 1990, also now abandoned.

TECHNICAL FIELD

The present invention relates generally to vaccines, and more specifically, relates to vaccines which may be utilized to prevent various forms of Leishmaniasis.

BACKGROUND OF THE INVENTION

Leishmaniasis is a tropical disease which is increasing in numbers not only in the tropics, but in moderate climates as well. Currently, between 50 and 75 million people suffer from this disease. Leishmanlasis is manifested in humans in three different forms, including visceral, mucocutaneous, and cutaneous forms. *Leishmania donovani* is the principal cause of visceral leishmaniasis, or kala-azar. The *L. donovani* organisms are usually present in endothelial cells of the blood and lymph capillaries, and in circulating macrophages. Additionally, they may be found in almost all organs, but occur especially in the spleen, liver, bone marrow, and lymph nodes.

*Leishmani braziliensis* causes mucocutaneous leishmaniasis or espundia. *L. braziliensis* organisms may be found in the skin, but most often migrate to secondary sites of infection in mucous membranes near cutaneous junctions.

In contrast, *Leishmania major* (formerly *Leishmania tropica*) affects only exposed areas of the skin rather than disseminating to various parts of the body. *L. major* first produce localized lesions which appear as a macule, then as a papule with a slightly raised center over a crater. Later the lesion opens at the center to discharge necrotic material. Forms of *Leishmania mexicana* are also believed to cause cutaneous leishmaniasis.

In general, the cutaneous manifestations vary from simple cutaneous lesions which persist for many months and eventually cure, to a disseminated form which is often refractory to chemotherapy and of significant clinical concern. Mucocutaneous forms have a latency period and can be therapeutically problematical, resulting in secondary disease proliferations. Without chemotherapy this disease is usually fatal. The latter is also true for visceral leishmaniasis, which is both difficult to diagnose and treat. Chemotherapy for the leishmanias is notably poor and not a practical solution for Third World countries. The ideal solution for all diseases of this type in a Third World setting is immunoprophylaxis. Treatment of leishmaniasis has generally involved the use of an antibiotic such as rifampicin, diamidine, or sodium antimony gluconante (Pentostam).

Immunity to the leishmaniasis is primarily of the cell mediated type, with an inconsequential contribution from antibody (see, Olobo, et al. "Antibodies to *Leishmania tropica* Promastigotes During Infection in Mice of Various Genotypes," *Aust. J. Exp. Biol. Med. Sci.* 58: 595, 1980; see also Hale C. and J. G. Howard, "Immunological Regulation of Experimental Cutaneous leishmaniasis. 2. Studies with Biozzi High and Low Responser Lines of Mice," *Parasite Immunol.* 3:45, 1981; and Howard et al., "Prophylactic Immunization Against Experimental Leishmaniasis. II. Further Characterization of the Protective Immunity Against Fatal *L. Tropica* Infection Induced by Irradiated Promastigotes," *J. Immunol.* 132:450, 1983). It has been shown that athymic routants of normally highly resistant CBA or C57BL mice are very susceptible to *Leishmania major* infections and that resistance to the parasite could be restored by adoptive transfer of syngeneic T-cells (see Mitchell et al., "Cutaneous Leishmaniasis in Mice: Disease Patterns in Reconstituted Nude Mice of Several Genotypes Infected with *L. tropica*," *Aust. J. Exp. Biol. Med. Sci.*, 58:521, 1980). Similarly, other studies have shown that acquired immunity to leishmaniasis may be transferred by T-cells but not by B-cells (see Liew et at., "Immunologic Regulation of Experimental Cutaneous Leishmaniasis," *J.. Immunol.* 128:1917, 1982).

Recent studies by Russell and Alexander have demonstrated that immunization of mice with proteoliposomes containing the major cell surface glycoprotein gp63, provided protection from subsequent challenges with virulent *L. mexicana* parasites (see Russell, D. G. and J. Alexander, "Effective Immunization Against Cutaneous Leishmaniasis with Defined Membrane Antigens Reconstituted into Liposomes," *J. Immunol.* 140:1274, 1988). Moreover, Russell and Alexander showed that adoptive transfer of T-cells from animals previously immunized with gp63 conferred protection against subsequent infection with the organism. One difficulty, however, of use of the intact glycoprotein by Russell and Alexander is that subcutaneous injections resulted in exacerbation rather than protection in the case of *L. major*.

The present invention provides vaccines against leishmaniasis, and further provides other related advantages.

SUMMARY OF THE INVENTION

Within one aspect of the present invention, an isolated immunogen is provided comprising a portion of the amino acid sequence as shown in FIG. 1 or a substantial equivalent thereof, wherein the immunogen exists in an oxidized form. Within various embodiments of the present invention, the following immunogens or substantial equivalents thereof may be utilized: (PT1) VRDVNWGALRIAVS; (PT2) LTNEKRDILVKHLIP; (PT3) YDQLVTRVVTHEMAHA; (PT4) TRVVTHEMAHALGFSG; (PT6) PFNVFSDAARCIDGAF; (PT7) AARCIDGAFRPKATDG; (PT8) RPKATDGIVKSYAGLC; (PT9) PQAVQLHTERLKVQQVQG; (PT10) VPSEEGVLAWATTCQ; (PT11) FSGPFFEDARIVANVP; (PT12) INSSTAVAKAREQYGC; (PT13) YGCDTLEYLEVEDQGG; (PT14) QDELMAPAAAAGYYTALTMA; (PT15) FGDLGFYQADFSKAEV; (PT16) SDGSCTQRASEAHASL; and (PT17) AKDGGNTAAGRRGPRA.

The present invention also provides a pharmaceutical composition comprising the above-described peptides or immunogens, in combination with a physiologically acceptable carrier or diluent.

Additionally, the present invention provides a method for stimulating an immune response in warm-blooded animals, comprising administering to the animal an effective mount of such a pharmaceutical composition.

These and other aspects of the present invention will become evident upon reference to the following detailed description and attached drawings.

BRIEF DESCRIPTION OF THE DRAWINGS

FIG. 1 illustrates the gp63 gene of *Leishmania major*. Immunogen sequences of the present invention are underlined.

DETAILED DESCRIPTION OF THE INVENTION

Figure 2A:
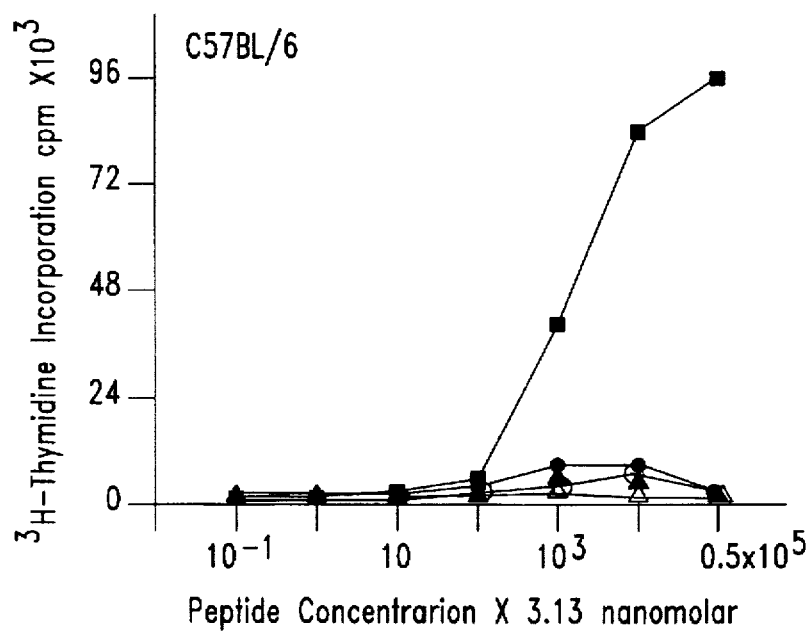
FIG. 2a–d illustrates T-cell proliferation dose response curves for seven synthetic peptides screened against four mouse strains with differing MHC haplotypes. Data represent averages of triplicate proliferation experiments after subtraction of average control proliferations. PT1 △—△, PT2 ▲—▲, PT3 ○—○, PT4 ●—●, PT6 ■—■, PT7 □—□, PT8 ◐—◐.
Figure 2B:
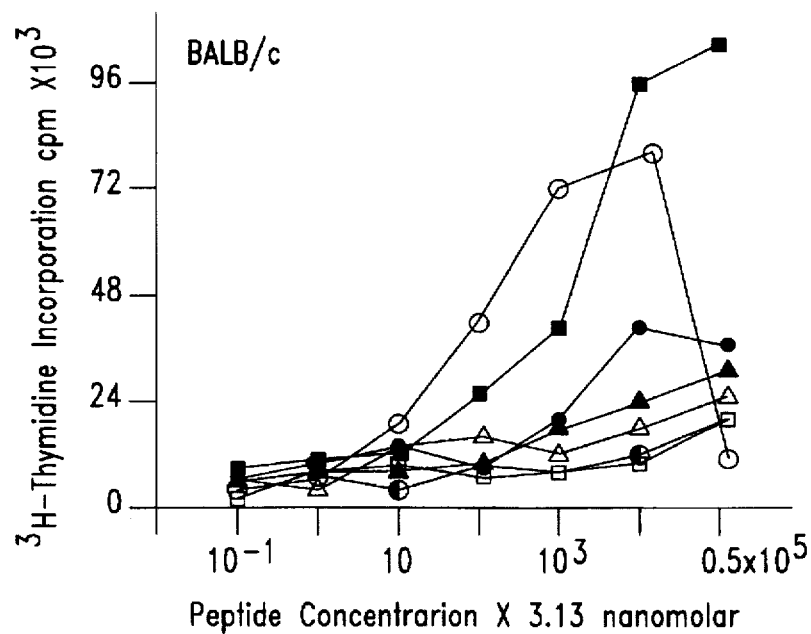
Figure 2C:
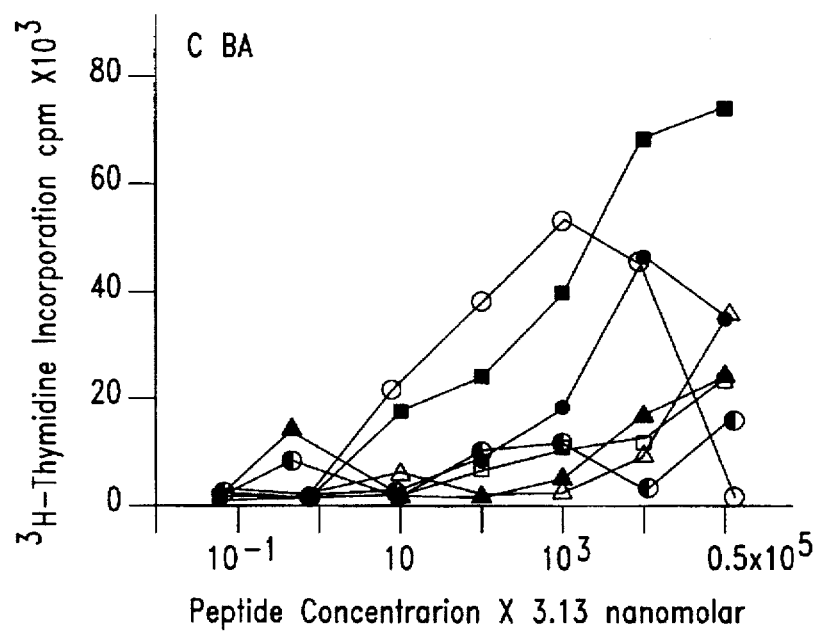
Figure 2D:
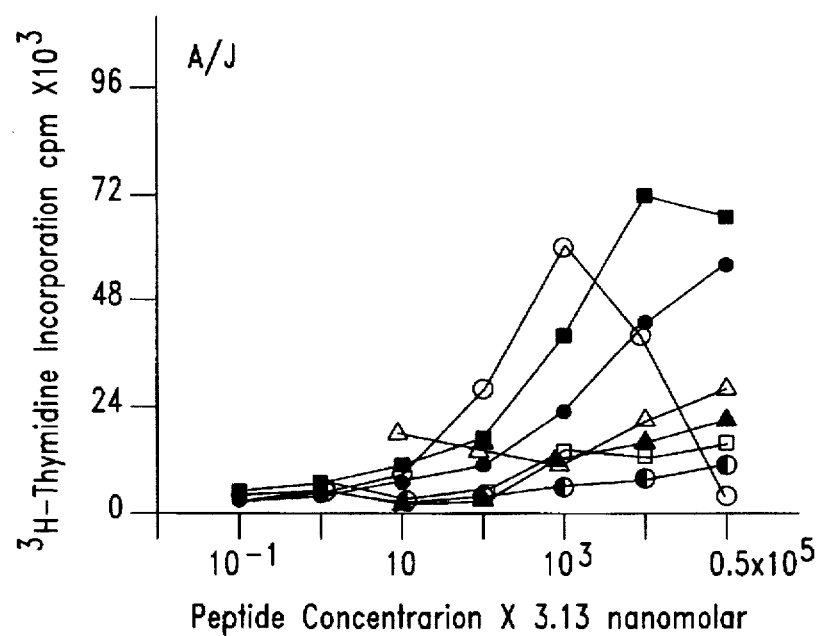

As noted above, within one aspect of the present invention isolated immunogens are provided comprising a portion of the amino acid sequence as shown in FIG. 1 or a substantial equivalent thereof, wherein the immunogen exists in an oxidized form. The immunogen is selected from the primary structure of L major, as described by Button and McMaster (see J. Exp. Med. 167:724, 1988)(see also FIG. 1). Various portions of the sequence according to FIG. 1 may be utilized within the context of the present invention. The immunogen may be selected from a portion of the amino acid sequence of FIG. 1 which is as small as 7 amino acids, and as large as about 40 to 50 amino acids, but preferably the portion will be about 12 to 35 amino acids in length. Portions which are particularly preferred are indicated as follows with the standard one-letter amino acid code: (PT1), VRDVNWGALRIAUS; (PT2), LTNEKRDILVKHHLIP; (PT3), YDQLVTRVVTHEMAHA; (PT4), TRVVTHEMAHALGFSG; (PT6), PFNVFSDAARCIDGAF; (PT7), AARCID-GAFRPKATDG; (PT8), RPKATDGIVKSYAGLC; (PT9), PQAVQLHTERLKVQQVQG; (PT10), VPSEEGVLAWATTCQ; (PT11), FSGPFFEDARIVANVP; (PT12), INSSTAVAKAREQYGC; (PT13), YGCDTLEYLEVEDQGG; (PT14), QDELMAPAAAAGYYTALTMA,; (PT15), FGDLGFYQADFSKAEV; (PT16), SDGSCTQRASEAHASL; and (PT17), AKDGGNTAAGRRGPRA.

As will be understood by one of ordinary skill in the art, slight deviations of the amino acid sequences may be made without affecting the immunogenicity of the immunogen. Substantial equivalents of the above peptides include conservative substitutions of amino acids which maintain substantially the same charge and hydrophobicity as the original amino acid. Conservative substitutions include replacement of valine for isoleucine, leucine or isoleucine, and aspartic acid for glutamic acid, as well as other substitutions of a similar nature. (See Dayhoff et al. (ed.), Atlas of Protein Sequence and Structure, natl. Biomed. Res. Fdn., 1978).

As will be evident to one of ordinary skill in the art, the immunogens listed above or their substantial equivalents may stimulate different levels of response in different animals, and may afford different degrees of protection for different species of Leishmania. Among other factors, HLA restriction is believed to be important in determining the degree of protection provided by a particular immunogen. Thus, the immunogens listed above or their substantial equivalents may be tested for effectiveness as a vaccine in experiments as described below in the Examples. These experiments include the T-cell proliferation assays, determination of lymphokine production after stimulation, and immunoprotection trials. Briefly, T-cell proliferation assays may be utilized as an indicator of potential for cell mediated immunity. Additionally, evidence of lymphokine production after stimulation by an immunogen may be utilized to determine the potential for protection provided by an immunogen. Recent findings have suggested that murine CD4$^+$T-cells are composed of at least two subsets which may be identified by differential lymphokine production. The Th1 subset produces IL2, IL3, and interferon gamma while the Th2 subset produced IL3 and IL4 (Mossmann et al., "Two Types of Murine Helper T-cell Clone: I. Definition According to Profiles of Lymphokine Activities and Secreted Proteins," Immunol. 8:223, ). Predominance of one or the other subset appears to be related to whether an immunoprotective or disease exacerbating condition is found following infection with Leishmania major (Locksley et al., "Murine Cutaneous Leishmaniasis: Susceptibility Correlates with Different Expansion of Helper T-Cell Subsets," Annales de l'Institut pasteur., Immunol. 138:738, 1987).

Finally, as described below, actual immunoprotection trials may be performed in order to determine protection in animals. In the case of humans however, instead of immunoprotection trials it is preferred to first screen peripheral blood lymphocytes from leishmaniasis patients in the following manner. Briefly, PBLs may be isolated from diluted whole blood using Ficoll density gradient centrifugation and utilized in cell proliferation studies with $^3$H-thymidine as described below. Positive peptides are selected and utilized in primate trials to study protection for both cutaneous and visceral forms of leishmaniasis.

The immunogens or peptides of the present invention may be readily produced utilizing many techniques well known in the art (see Sambrook et al., Molecular Cloning, A Laboratory Manual, Cold Spring Harbor Laboratory Press, 1989). Particularly preferred is the synthesis of the immunogens utilizing conventional peptide synthesizers. As noted above, in the most preferred embodiment the immunogen is left in an oxidized state, rather than being reduced. More specifically, the methionine residues must be in the oxidized form; this is similar to the exposure of antigen to peroxides present in the macrophage phagolysosomal vacuole.

Administration of Immunogens

The present invention provides methods for simulating an immune response in warm-blooded animals comprising administering an effective amount of a pharmaceutical composition comprising an immunogen, and a physiologically acceptable carrier or diluent. For purposes of the present invention, warm-blooded animals include, among others, humans, primates, dogs, cats, pigs, sheep, horses, rats and mice.

Many suitable carriers or diluents may be utilized in the present invention, including among others saline, buffered saline, and saline mixed with nonspecific serum albumin. The pharmaceutical composition may also contain other excipient ingredients, including adjuvants, buffers, antioxidants, carbohydrates such as glucose, sucrose, or dextrins, and chelating agents such as EDTA. Within a particularly preferred embodiment, an adjuvant is utilized along with the immunogen. Particularly preferred adjuvants include alum or aluminum hydroxide for humans, and Poloxamer 407 for dogs. The choice of adjuvant plays an important role in the development of protection against Leishmania, and should be determined in immunoprotection trials.

The amount and frequency of administration may be determined in clinical trials, and will depend upon such factors as the animal to be vaccinated, its HLA type, the Leishmania species against which it is desired to protect, the particular immunogen used, the degree of protection required, as well as many other factors. Preferably, immunizations will involve parenteral administration via the subcutaneous route. Depending upon the application, veterinary or clinical (human), quantifies of injected immunogen will vary from 100 µg to several milligrams in an adjuvant vehicle. Booster immunizations may be given from 4–6 weeks later.

The following examples are offered by way of illustration, and not by way of limitation.

EXAMPLES

Example 1

Synthesis of Immunogens or Peptides

Immunogens or peptides were synthesized using standard Merrifield solid phase technology using benzylhydrylamine resin on an automated peptide synthesizer (Applied Biosystems Incorporated Model 430A). Methionine peptides were left in the methionine sulfoxide form and not reduced. Purification was carried out by organic extraction and reverse phase HPLC. The following peptides were synthesized: PT1, VRDVNWGALRIAUS; PT2, LTNEKRDIL-VKHLIP; PT3, YDQLVTRVVTHEMAHA; PT4, TRV-VTHEMAHALGFSG; PT6, PFNVFSDAARCIDGAF; PT7, AARCIDGAFRPKATDG; PT8, RPKATDGIVKSYA-GLC; PT9, PQAVQLHTERLKVQQVQG; PT10, VPSEE-GVLAWATTCQ; PT11, FSGPFFEDARIVANVP; PT12, INSSTAVAKAREQYGC; PT13, YGCDTLEY-LEVEDQGG; PT14, QDELMAPAAAAGYYTALTMA; PT15, FGDLGFYQADFSKAEV; PT16, SDG-SCTQRASEAHASL; PT17, AKDGGNTAAGRRGPRA. The peptides represent gp63 residues 1–14 (PT1), 48–62 (PT2), 62–79 (PT9), 117–131 (PT10), 154–169 (PT3), 159–174 (PT4), 172–187 (PT11), 199–214 (PT12), 212–227 (PT13), 241–260 (PT14), 262–277 (PT15), 362–377 (PT16), 379–394 (PT6), 386–401 (PT7), 395–410 (PT8), and 472–487 (PT17). Immunogen compositions were confirmed by amino acid analysis.

Example 2

T-Cell Proliferation Assays

The ability of some of the above immunogens to stimulate lymphocyte proliferation was tested by immunization of mice, followed by in vitro challenge of isolated lymph node cells with the test immunogens (see FIG. 2). Three mice were inoculated subcutaneously with 50 µg of peptide emulsified in 100 µl of Freund's complete adjuvant. Lymph nodes were removed after 9 days and 5×10[5] cells incubated for 3 days with synthetic peptides followed by further incubation for 20 hours with 1 µCi $^3$H-thymidine. Control B-cell proliferations used 20 µg/ml of E. coli lipopolysaccharide (LPS). Lymphocyte stimulation was plotted as the average counts per minute (cpm) of triplicate experimental cultures minus the average of the relevant triplicate control values. Each of the proliferation experiments were replicated at least twice.

Figure 3A:
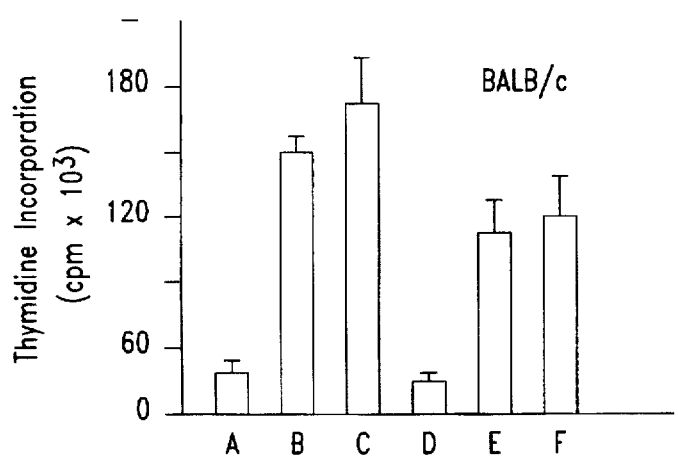
FIG. 3a–c is a graph illustrating the effect of anti-L3T4+ (CD4$^+$) and anti-Lyt-2.2$^+$(CD8+) monoclonal antibodies and rabbit complement on PT6 stimulation of primed lymphocytes. Lanes A and B; lymph node cells from immunized mice incubated with anti-L3T4$^+$, or anti-Lyt-2.2$^+$MAb and rabbit complement followed by PT6 (156 μM). Lane C is complement alone followed by peptide. Lane D is no additions. Lane E is LPS induced proliferation and lane F is LPS proliferation after exposure to anti-L3T4$^+$antibody and complement.
Figure 3B:
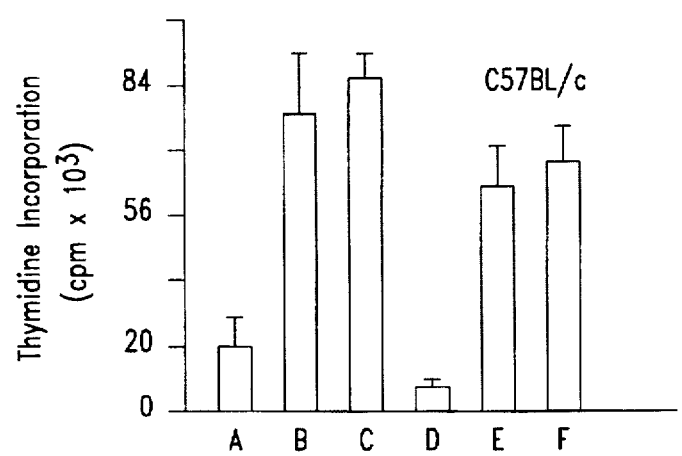
Figure 3C:
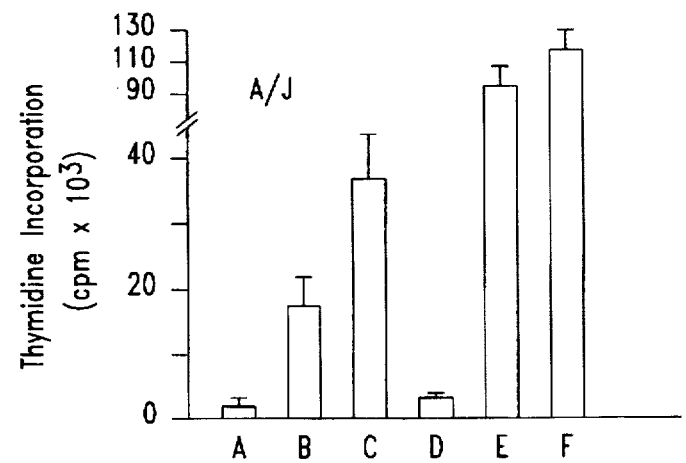

Verification that $^3$H-thymidine incorporation was associated with T-cell proliferation was provided by T-cell specific depletion using anti-Thy-1 antisera (Table 1) or anti-L3T4+ monoclonal antibody and complement (FIG. 3). Lysis was carried out using 5×10$^5$ lymph node cells incubated with either alloanti-Thy-1 antisera, anti-L3T4$^+$or anti-Lyt-2.2$^+$ monoclonal antibodies (Cederlane Laboratories Ltd., Hornby, Ontario) for 60 minutes at 4° C. followed by addition of 10% rabbit complement for 60 minutes at 37° C. While only data for the peptide PT6 is shown, similar proliferation data were obtained for peptides PT3 and PT4 and in experiments with lymphocytes from the other responding mouse strains. These data show that the proliferating cells are primarily of the CD$^+$subset. Evidence was also obtained that the B-cell population was unaffected by the depletion procedure by employing the B-cell mitogen LPS (FIG. 3).

TABLE 1

| | $^3$H-Thymidine Incorporation* | | | |
|---|---|---|---|---|
| | Challenge peptide - PT6 Concentration (µM) | | | |
| Treatment | 31.3 | 3.1 | 0.3 | Con A |
| Anti-Thy1 + Complement | 1.4 ± 0.3 | 3.5 ± 0.6 | 3.2 ± 0.2 | 2.5 ± 0.3 |
| Complement Alone | 41.2 ± 3.6 | 43.7 ± 2.4 | 29.1 ± 2.0 | 43.0 ± 8.0 |
| None | 76.2 ± 8.2 | 56.7 ± 6.7 | 20.8 ± 1.2 | ND |

*The average thymidine incorporation in the absence of peptide (16.2 ± 2.2 cpm) has been subtracted from the above data.

FIG. 2 depicts dose response curves following challenge of primed lymph node cells with the immunizing peptides. Data represent averages of triplicate proliferation experiments after subtraction of average control proliferations. The average control values were: C57BL/6, 6.8×10$^3$ cpm; BALB/c, 11.6×10$^3$ cpm; CBA, 21.8×10$^3$ cpm and A/J, 8.4×10$^3$ cpm. PT1 △—△, PT2 ▲—▲, PT3 ○—○, PT4 ●—●, PT6 ■—■, PT7 □—□, △—△, PT8◐—◐. Three peptides were found to be stimulatory. The overlapping peptides PT3 and PT4, which cover a highly conserved region believed to be responsible for zinc binding (Chaudhuri et al., "Surface Acid Proteinase (gp63) of Leishmania mexicana," J. Biol. Chem. 264:7483, 1989; see also Bouvier et al., "Characterization of the Promastigote Surface Protease of Leishmania as a Membrane-Bound Zinc Endopeptidase," Mol. Biochem. Parasitol. 37:235 1989), stimulated proliferation in cells derived from BALB/c (H-2$^d$), A/J (H-2$^a$) and CBA (H-2$^k$) mice but not in C57BL/6 (H-2$^b$) lymphocytes. Peptide PT6 was panspecific for this collection of mouse haplotypes, stimulating lymphocytes from all strains.

FIG. 3 as illustrated above illustrates the effect of anti-L3T4+(CD4$^+$) and anti-Lyt-2.2$^+$(CD8$^+$) monoclonal antibodies and rabbit complement on PT6 stimulation of primed lymphocytes. Lanes A and B illustrate lymph node cells from immunized mice incubated with anti-L3T4$^+$, or anti-Lyt-2.2$^+$MAb and rabbit complement followed by PT6 (156 µM). Lane C is complement alone followed by peptide. Lane D is no additions. Lane E is LPS induced proliferation and lane F is LPS proliferation after exposure to anti-L3T4$^+$ antibody and complement.

Example 3

Lymphokine Determinations

A study of lymphokine production, after challenge of lymph node cells with the stimulatory peptides showed that only PT3 was capable of stimulating IL2 (Table 2) and that none of the epitopes produced measurable IL4.

Briefly, interleukin 2 (IL2) and interleukin 4 (IL4) were assayed using the IL2 and IL4 dependent CTLL-2 cell line (ATTC TIB 214). Specific neutralization was achieved with an anti-IL2 antibody, S4B6 (17) or with the anti-IL4 antibody, 11B11 (ATCC HB). IL3 was determined using the IL3 dependent cell line DA-1. Results were expressed as units of lymphokine extrapolated from standard recombinant interleukin curves.

Thus, under the immunization protocol used, PT3 specifically induced proliferation of the CD4$^+$Th1 subset (see Mosman et al., "Two Types of Murine Helper T-Cell Clone—I. Definition According to Profiles of Lymphokine Activities and Secreted Proteins," *J. Immunol.* 8:223, 1986).

TABLE 2

Lymphokine production following stimulation of T-cells from BALB/c and CBA mice with synthetic gp63 peptides.

| | Lymphokine (Units/ml)* | | | | | |
|---|---|---|---|---|---|---|
| | IL2 | | IL3 | | IL4 | |
| Challenge Peptide | BALB/c | CBA | BALB/c | CBA | BALB/c | CBA |
| PT3 | 0.8 | 1.9 | 3.8 | ND | 0 | 0 |
| PT4 | 0 | 0 | 0.3 | ND | 0 | 0 |
| PT6 | 0 | 0 | 7.0 | ND | 0 | 0 |
| No Peptide | 0 | 0 | 0 | 0 | 0 | 0 |

*Zero values indicate no detectable lymphokine; ND indicates not done.

Example 4

Immunoprotection Trials

Four groups of 8 female BALB/c mice were used in this study. Mice were purchased from either Jackson Laboratories, Bar Harbour, Me. or from the Charles River Breeding Laboratories, St. Constant, Quebec and used at 8–10 weeks of age. BALB/c mice for immunoprotection trials were bred in house. Each group was injected subcutaneously with 100 µg of PT3, PT4, or PT6 in a temperature dependent sol gel transition adjuvant, 8% Poloxamer 407, (BASF, Wayandotte, Ludwigshaven, Germany) with the exception of the control group which received only adjuvant. After 6 weeks the mice were inoculated subcutaneously in the hind quarters with 2×10$^4$ stationary phase *L. major* promastigotes. A similar study utilized *L. mexicana* promastigotes and CBA mice. Progress of disease was monitored by measurement of lesion diameter beginning at 4 weeks after inoculation.

Figure 4:
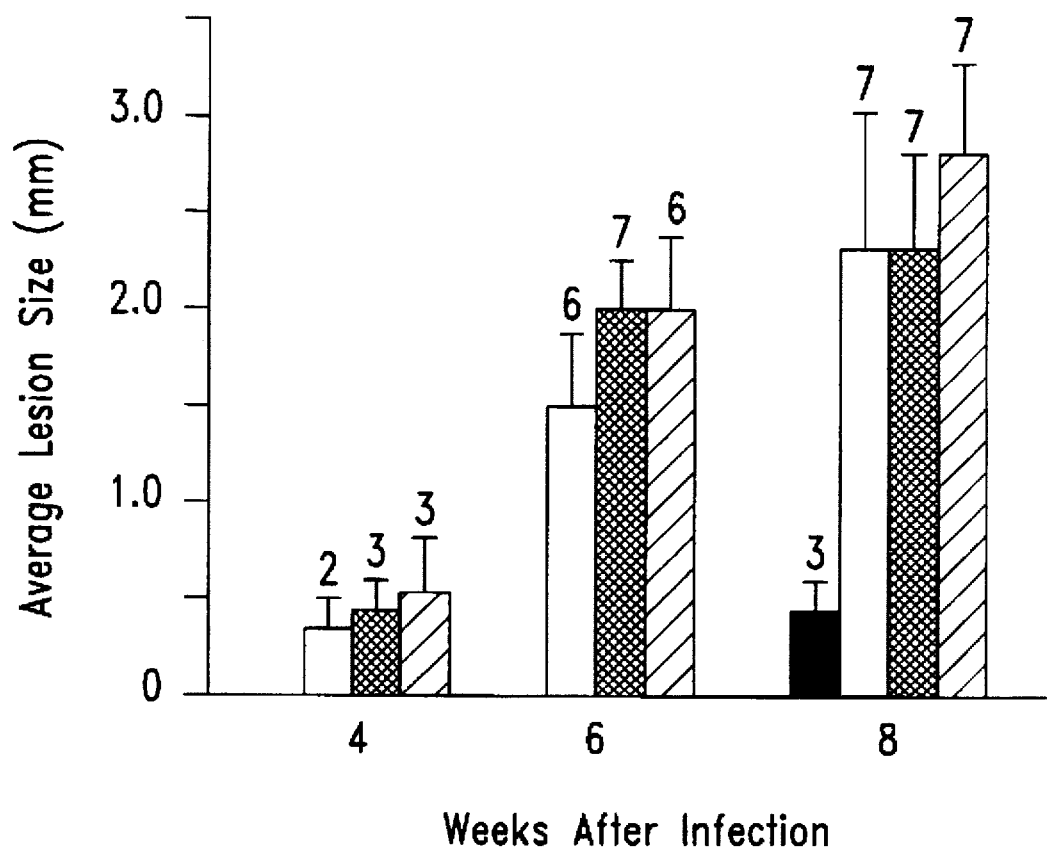
FIG. 4 illustrates the development of L. major infection in groups of 8BALB/c mice after immunization with synthetic peptides. Lesion diameters are shown above each bar along with the standard error of the mean. Controls receiving adjuvant only, hatched bar; PT3, solid bar; PT4, open bar; PT6, shaded bar.

FIG. 4 illustrates the development of *L. major* infection. Lesion diameters are shown above each bar along with the standard error of the mean. Controls receiving adjuvant only are represented by a hatched bar; PT3 by a solid bar; PT4 by an open bar; and PT6 by a shaded bar. Lesion development was evident at 4 weeks in control animals, as well as in animals inoculated with PT4 and PT6 but not in the group immunized with PT3. At 6 weeks the number of infected animals in previously infected groups increased, along with the average lesion size, while no evidence of infection could be found in the group immunized with PT3 plus adjuvant. Not until two months post inoculation was there evidence of lesion development in the latter group. This appeared to be the end of a period of premunition induced by the single subcutaneous injection of antigen. A second experiment (not shown), utilizing the same protocol but with a slightly higher adjuvant concentration (12.5%), provided further verification of the immunoprotective capacity of PT3. Not only was this peptide once again shown to limit the disease but half the animals vaccinated with PT3 cured of disease 12 to 16 weeks after inoculation with parasites. Results using *Leishmania mexicana* and the previous protocol (not shown) were even more convincing, with complete lack of disease in the vaccinated group 3 months after parasite challenge.

That these findings were not entirely related to the Poloxamer 407 adjuvant was shown by conducting another *L. major* experiment but replacing Poloxamer with Freund's complete adjuvant. No sign of disease was found in vaccinated animals 5 weeks after parasite inoculation while all controls showed lesion development. Nonetheless an interesting result from the second *L. major* experiment with Poloxamer indicated that the use of adjuvant was an important determinant in the outcome of these subcutaneous vaccinations. When PT3 was injected in the absence of adjuvant an exacerbation in lesion growth was observed (data not shown). This result mimicked a previously described disease exacerbation produced in BALB/c mice following subcutaneous vaccination with irradiated *L. major* promastigotes (Liew et al., "Prophylactic Immunization Against Experimental Leishmaniasis. IV. Subcutaneous Immunization Prevents the Induction of Protective Immunity Against Fatal *Leishmania Major* Infection," *J. Immunol.* 135:2095, 1985; see also, Liew et al., "Prophylactic Immunization Against Experimental Leishmaniasis. V. Mechanism of the Anti-Protective Blocking Effect Induced by Subcutaneous Immunization against *Leishmania major* Infection," *J. Immunol.* 135:2102, 1985).

From the foregoing, it will be appreciated that, although specific embodiments of the invention have been described herein for purposes of illustration, various modifications may be made without deviating from the spirit and scope of the invention. Accordingly, the invention is not limited except as by the appended claims.

I claim:

1. An isolated immunogen PT1 having the sequence VRDVNWGALRIAVS or a substantial equivalent thereof.

2. An isolated immunogen PT3 having the sequence YDQLVTRVVTHEMAHA or a substantial equivalent thereof.

3. An isolated immunogen PT4 having the sequence TRVVTHEMAHALGFSG or a substantial equivalent thereof.

4. An isolated immunogen PT7 having the sequence AARCIDGAFRPKATDG or a substantial equivalent thereof.

5. An isolated immunogen PT8 having the sequence RPKATDGIVKSYAGLC or a substantial equivalent thereof.

6. An isolated immunogen PT11 having the sequence FSGPFFEDARIVANVP or a substantial equivalent thereof.

7. A pharmaceutical composition comprising the immunogen according to any one of claims 1, 2, 3, 4, 5, or 6 and a physiologically acceptable carrier or diluent.

8. A method for stimulating an immune response in warm-blooded animals, comprising administering an effective amount of the pharmaceutical composition according to claim 7 to the animal.

* * * * *

UNITED STATES PATENT AND TRADEMARK OFFICE
CERTIFICATE OF CORRECTION

PATENT NO. : 5,674,503

DATED : October 7, 1997

INVENTOR(S) : Robert W. Olafson

It is certified that error appears in the above-identified patent and that said Letters Patent is hereby corrected as shown below:

In column 6, line 44, please delete "Δ-Δ".

In column 8, claim 1, line 44, please delete "PT1 having" and insert therefor --up to 50 amino acids and containing--.

In column 8, claim 1, line 45, please delete "or a substantial equivalent thereof".

In column 8, claim 2, line 46, please delete "PT3 having" and insert therefor --up to 50 amino acids and containing--.

In column 8, claim 2, line 47, please delete "or a substantial equivalent thereof".

In column 8, claim 3, line 49, please delete "PT4 having" and insert therefor --up to 50 amino acids and containing--.

In column 8, claim 3, line 50, please delete "or a substantial equivalent thereof".

In column 8, claim 4, line 52, please delete "PT7 having" and insert therefor --up to 50 amino acids and containing--.

UNITED STATES PATENT AND TRADEMARK OFFICE
CERTIFICATE OF CORRECTION

PATENT NO. : 5,674,503
DATED : October 7, 1997
INVENTOR(S) : Robert W. Olafson

It is certified that error appears in the above-identified patent and that said Letters Patent is hereby corrected as shown below:

In column 8, claim 4, line 53, please delete "or a substantial equivalent thereof".

In column 8, claim 5, line 55, please delete "PT8 having" and insert therefor --up to 50 amino acids and containing--.

In column 8, claim 5, line 56, please delete "or a substantial equivalent thereof".

In column 8, claim 6, line 58, please delete "PT11 having" and insert therefor --up to 50 amino acids and containing--.

In column 8, claim 6, line 59, please delete "or a substantial equivalent thereof".

Signed and Sealed this

Tenth Day of February, 1998

Attest:

BRUCE LEHMAN

Attesting Officer       Commissioner of Patents and Trademarks